(12) United States Patent
Ruelas et al.

(10) Patent No.: US 9,689,830 B2
(45) Date of Patent: Jun. 27, 2017

(54) SENSOR DETECTION PADS WITH INTEGRATED FUSE

(71) Applicant: Medtronic MiniMed, Inc., Northridge, CA (US)

(72) Inventors: Jose J. Ruelas, San Fernando, CA (US); David Y. Choy, San Gabriel, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 436 days.

(21) Appl. No.: 14/244,132

(22) Filed: Apr. 3, 2014

(65) Prior Publication Data

US 2015/0285757 A1 Oct. 8, 2015

(51) Int. Cl.
| | |
|---|---|
| G01N 15/06 | (2006.01) |
| G01N 33/00 | (2006.01) |
| G01N 33/48 | (2006.01) |
| G01N 27/00 | (2006.01) |
| G01N 31/00 | (2006.01) |
| G01N 33/50 | (2006.01) |
| G01N 27/327 | (2006.01) |

(52) U.S. Cl.
CPC ................. *G01N 27/327* (2013.01)

(58) Field of Classification Search
CPC ........ G01N 15/06; G01N 33/00; G01N 33/48; G01N 27/00; G01N 31/00; G01N 33/50
USPC ................. 422/68.1, 82.01, 82.02, 502, 503; 600/300, 316, 347, 365; 204/403.11; 436/43, 95
See application file for complete search history.

(56) References Cited

U.S. PATENT DOCUMENTS

| | | | |
|---|---|---|---|
| 4,755,173 A | 7/1988 | Konopka et al. | |
| 5,391,250 A | 2/1995 | Cheney, II et al. | |
| 5,485,408 A | 1/1996 | Blomquist | |
| 5,522,803 A | 6/1996 | Teissen-Simony | |
| 5,665,065 A | 9/1997 | Colman et al. | |
| 5,800,420 A | 9/1998 | Gross et al. | |
| 5,807,375 A | 9/1998 | Gross et al. | |
| 5,925,021 A | 7/1999 | Castellano et al. | |
| 5,954,643 A | 9/1999 | Van Antwerp et al. | |
| 6,001,067 A * | 12/1999 | Shults et al. | .................. 600/584 |
| 6,017,328 A | 1/2000 | Fischell et al. | |
| 6,186,982 B1 | 2/2001 | Gross et al. | |
| 6,246,992 B1 | 6/2001 | Brown | |
| 6,248,067 B1 | 6/2001 | Causey, III et al. | |
| 6,248,093 B1 | 6/2001 | Moberg | |
| 6,355,021 B1 | 3/2002 | Nielsen et al. | |
| 6,379,301 B1 | 4/2002 | Worthington et al. | |

(Continued)

*Primary Examiner* — Brian J Sines
(74) *Attorney, Agent, or Firm* — Medtronic Minimed, Inc.

(57) ABSTRACT

A monitor system to monitor a characteristic of a user is disclosed. A monitor system includes a sensor producing signals indicative of glucose characteristics within the user. The sensor has a connector with a plurality of contacts, at least two contacts being shorted by a fuse trace. The monitor system further includes an electronics package with a package housing. The package housing contains a battery, a package port interfaced with the connector to receive signals from the sensor, and a package processor to process the signals from the sensor. Further included in the monitor system is a fuse system controlled by the package processor that includes a fuse timer, wherein the fuse trace is destroyed after the fuse timer reaches a threshold value.

11 Claims, 9 Drawing Sheets

(56) References Cited

U.S. PATENT DOCUMENTS

| | | |
|---|---|---|
| 6,544,212 B2 | 4/2003 | Galley et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 2005/0096587 A1* | 5/2005 | Santini et al. .................. 604/66 |
| 2005/0235732 A1* | 10/2005 | Rush .............................. 73/1.16 |
| 2007/0123819 A1 | 5/2007 | Mernoe et al. |
| 2010/0160861 A1 | 6/2010 | Causey, III et al. |

\* cited by examiner

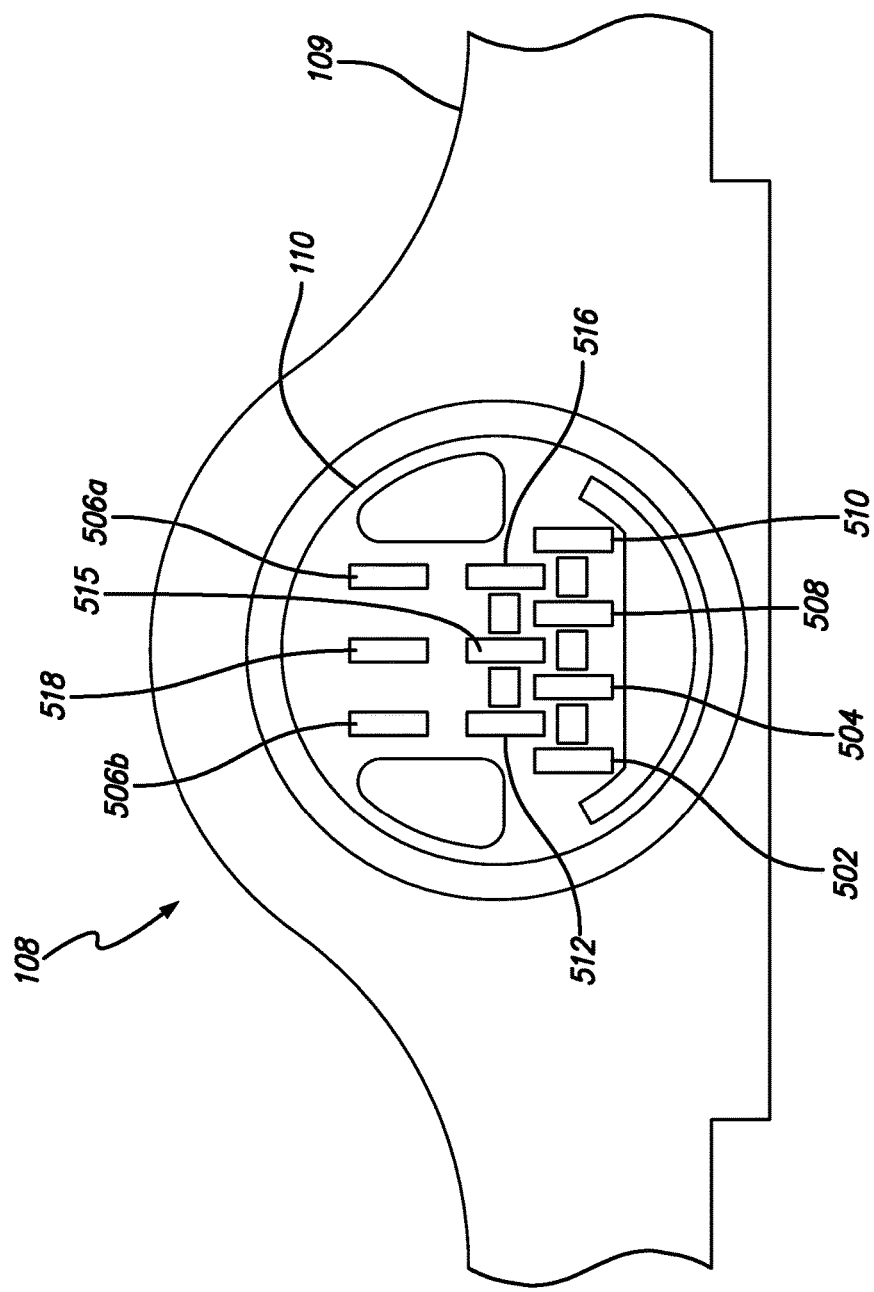

US 9,689,830 B2

SENSOR DETECTION PADS WITH INTEGRATED FUSE

FIELD OF THE INVENTION

This invention relates to monitor systems and, in particular embodiments, to devices and methods for operation of a sensor to determine a characteristic of a body.

BACKGROUND OF THE INVENTION

Over the years, bodily characteristics have been determined by obtaining a sample of bodily fluid. For example, diabetics often test for blood glucose levels. Traditional blood glucose determinations have utilized a painful finger prick using a lancet to withdraw a small blood sample. This results in discomfort from the lancet as it contacts nerves in the subcutaneous tissue. The pain of lancing and the cumulative discomfort from multiple needle pricks is a strong reason why patients fail to comply with a medical testing regimen used to determine a change in characteristic over a period of time. Although non-invasive systems have been proposed, or are in development, none to date have been commercialized that are effective and provide accurate results. In addition, all of these systems are designed to provide data at discrete points and do not provide continuous data to show the variations in the characteristic between testing times.

A variety of implantable electrochemical sensors have been developed for detecting and/or quantifying specific agents or compositions in a patient's blood. For instance, glucose sensors have been developed for use in obtaining an indication of blood glucose levels in a diabetic patient. Such readings are useful in monitoring and/or adjusting a treatment regimen which typically includes the regular administration of insulin to the patient. Thus, blood glucose readings improve medical therapies with semi-automated medication infusion pumps of the external type, as generally described in U.S. Pat. Nos. 4,562,751; 4,678,408; and 4,685,903; or automated implantable medication infusion pumps, as generally described in U.S. Pat. No. 4,573,994, which are herein incorporated by reference. Typical thin film sensors are described in commonly assigned U.S. Pat. Nos. 5,390,671; 5,391,250; 5,482,473; and 5,586,553 which are incorporated by reference herein, also see U.S. Pat. No. 5,299,571. However, the monitors for these continuous sensors provide alarms, updates, trend information and require sophisticated hardware to allow the user to program the monitor, calibrate the sensor, enter data and view data in the monitor and to provide real-time feedback to the user. This sophisticated hardware makes it most practical for users that require continuous monitoring with feedback to maintain tight control over their conditions. In addition, these systems require the user to be trained in their use, even if to be worn for short periods of time to collect medical data which will be analyzed later by a doctor.

Doctors often need continuous measurements of a body parameter over a period of time to make an accurate diagnosis of a condition. For instance, Holter monitor systems are used to measure the EKG of a patient's heart over a period of time to detect abnormalities in the heart beat of the patient. Abnormalities detected in this manner may detect heart disease that would otherwise go undetected. These tests, while very useful are limited to monitoring of bio-mechanical physical changes in the body, such as a heart beat, respiration rate, blood pressure or the like.

Electrochemical sensors typically have a well-defined finite time of use. Contributing to the finite life is the consumption or reaction of chemical reagents that allow the sensor to detect the desired agents and compositions. Upon consumption of the sensor reagents it is possible to get spurious or inaccurate readings from a sensor. It is therefore undesirable and even potentially dangerous to use a sensor beyond its designed lifetime. Despite the known dangers, there are documented cases of sensors being used well beyond their design lifetime. In order to provide accurate data and optimized care, it would be beneficial to have a sensor capable of turning itself off after a specified design lifetime has elapsed.

SUMMARY OF THE DISCLOSURE

In one embodiment a monitor system to record a characteristic of a user is disclosed. The monitor system includes a sensor to produce signals indicative of a glucose characteristic measured in the user. The sensor includes a connector with a plurality of contacts where at least two of the contacts being shorted by a fuse trace. The system further includes an electronics package that includes a package housing that contains, a battery, a package port interfaced with the connector to receive signals from the sensor, and a package processor to process the signals from the sensor and store the processed signals in non-volatile memory. Further included in the package housing is a fuse system controlled by the package processor that includes a fuse timer. Wherein the fuse trace is destroyed after the fuse timer reaches a threshold value.

In another embodiment a monitor system to transmit a real-time characteristic of a user is disclosed. The monitor system includes a sensor to produce signals indicative of a glucose characteristic measured in the user, the sensor having a connector with a plurality of contacts, at least two contacts being shorted by a fuse trace; and an electronics package that includes a package housing, a battery being contained within the package housing, a package port interfaced with the connector to receive the produced signals from the sensor, a package processor to process the produced signals from the sensor and transmit the processed signals via a transmitter, a fuse system controlled by the package processor that includes a fuse timer; wherein the fuse trace is destroyed after the fuse timer reaches a threshold value.

Other features and advantages of the invention will become apparent from the following detailed description, taken in conjunction with the accompanying drawings which illustrate, by way of example, various features of embodiments of the invention.

BRIEF DESCRIPTION OF THE DRAWINGS

A detailed description of embodiments of the invention will be made with reference to the accompanying drawings, wherein like numerals designate corresponding parts in the several figures.

FIG. 5A is an exemplary illustration of package port that would receive the connector from the sensor, in accordance with one embodiment of the present invention.

DETAILED DESCRIPTION

Figure 1:
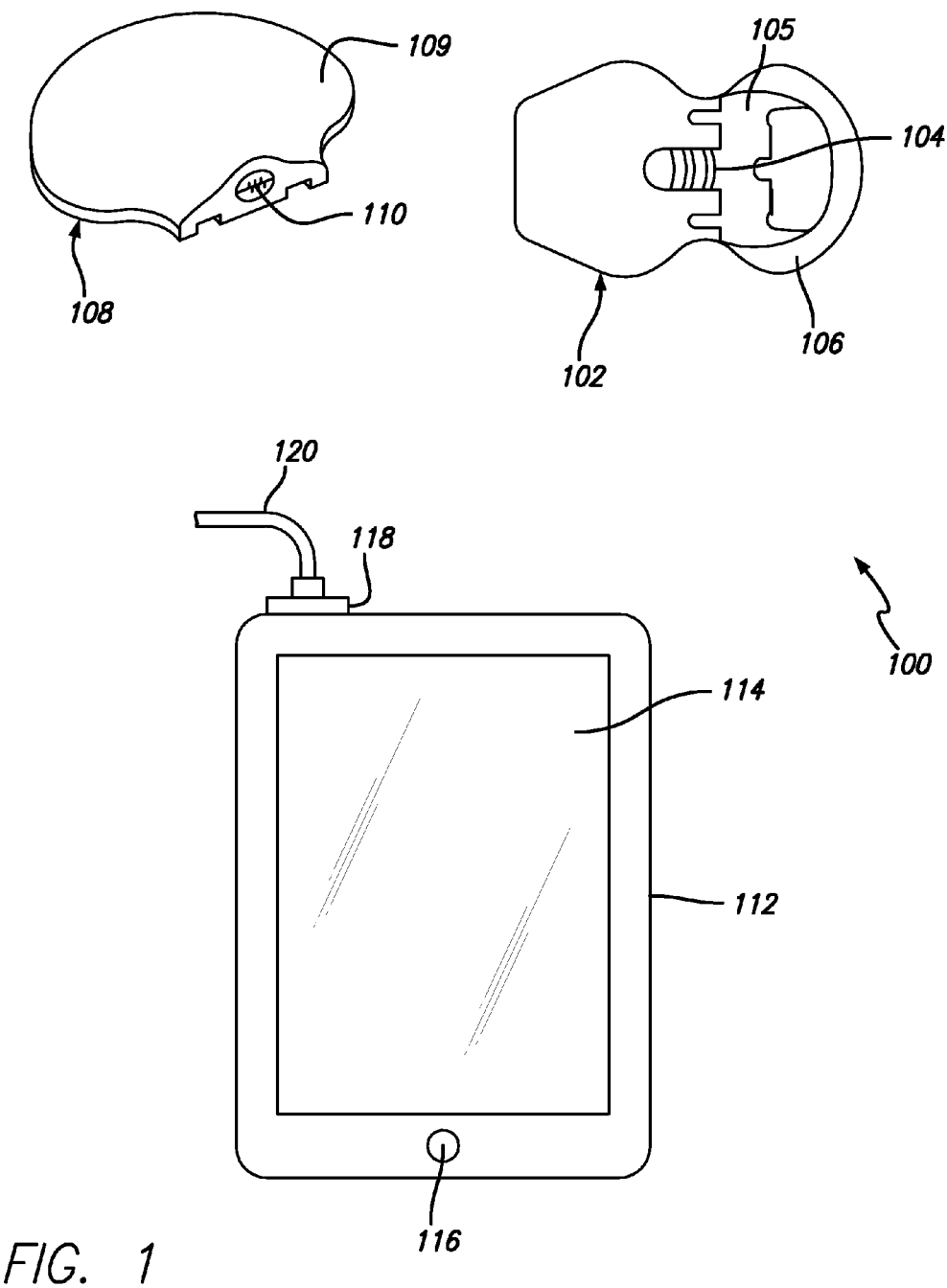
FIG. 1 is an exemplary illustration of components of a monitor system, in accordance with embodiments of the present invention.

As shown in the drawings for purposes of illustration, the invention is embodied as a component within a subcutaneous implantable analyte sensor set that provide continuous data of the sensor readings to a portable infusion system. In some embodiments the sensor data is recorded into memory integrated into an electronics package that also provides power and wireless communication capability to the sensor. In other embodiments the sensor transmits sensor readings to an infusion pump that can include memory to store the sensor readings. The recorded sensor readings or data can later be downloaded or transferred to a computing device to determine body characteristic data based on the data recording over the period of time. In embodiments of the present invention, the analyte sensor set and monitor system are for determining glucose levels in the blood and/or bodily fluids of the user without the use of, or necessity of, complicated monitoring systems that require user training and interaction. However, it will be recognized that further embodiments of the invention may be used to determine the levels of other analytes or agents, characteristics or compositions, such as hormones, cholesterol, medications concentrations, viral loads (e.g., HIV), or the like. In other embodiments, the monitor system may also include the capability to be programmed to record data at specified time intervals. The monitor system and analyte sensor are primarily adapted for use in subcutaneous human tissue. However, still further embodiments may be placed in other types of tissue, such as muscle, lymph, organ tissue, veins, arteries or the like, and used in animal tissue. The analyte sensors may be subcutaneous sensors, transcutaneous sensors, percutaneous sensors, sub-dermal sensors, skin surface sensors, or the like. Embodiments may measure and record sensor readings on an intermittent or continuous basis.

FIG. 1 is an exemplary illustration of components within a monitor system 100, in accordance with embodiments of the present invention. The sensor 102 is shown from an exemplary top view as if it has been inserted into a patient. In one embodiment the sensor 102 utilizes an electrode-type sensor while in alternative embodiments, the sensor 102 may use other types of sensors, such as chemical based, optical based or the like. In further alternate embodiments, the sensor 102 may be of a type that is used on the external surface of the skin or placed below the skin layer of the user or placed in the blood stream of the user. Other embodiments of a surface mounted sensor would utilize interstitial fluid harvested from the skin.

In some embodiments, the sensor 102 is an assembly commonly known as a "sensor set" that includes, but it not limited to the connector 104, sensor adhesive (not shown) covered by an adhesive backing 106, an introducer needle (not shown in FIG. 1), a sensing portion of the sensor to be placed in a body (not shown), and a mounting base 105. In one embodiment the connector 104 is integrally injection molded from plastic with the mounting base 105. The connector 104 further includes electrical contacts that interface with contacts on the sensor. On a side opposite that shown in FIG. 1, the adhesive is applied to the mounting base 105 and the adhesive backing 116 is further applied over the adhesive.

An electronic package 108 is also included in the monitor system 100. The electronics package 108 includes a package housing 109 with a package port 110. The package port 110 is designed to couple with the electrical contact on the connector 104 thereby providing power and other electrical interfaces between the electronics package 108 and the sensor 102. In one embodiment the electronics package further includes a power source, processor and transmitter within the package housing 109. The power source provides power for the processor and transmitter and when coupled to the connector 104, further powers the sensor 102. In such an embodiment signals generated by an installed sensor can be processed via the processor and transmitted to another device such as, but not limited to infusion pump 112. In other embodiments, the electronics package 108 includes at least a power source, processor, transmitter along with memory and a receiver. In these embodiments sensor signals from an installed sensor can be stored to memory within the package housing 109 and periodically transmitted to the infusion pump 112 or other devices configured to communicate with the electronics package 108. Additionally, the inclusion of the receiver within the electronics package would enable two-way communication between other devices and the electronics package 108.

The inclusion of memory within the electronics package 108 can enable the combined electronics package 108 and sensor 102 to be used as a Holter-type recording device that can use the package port 110 to interface with either the sensor 102 or a docking station (not shown) that is further connected to a computer of tablet computing device. When used as a recording device the combined electronics package 108 and sensor 102 have the capability to record and store data as it is received from the sensor 102. When the electronics package 108 is coupled to a docking station the data stored on the memory of the electronics package 108 can be transferred to networked or local data storage and analyzed using general computing processors such as desktops, laptops, notebooks, netbooks, tablets, or handheld computing devices such as, but not limited to smart phones and the like. To enable data transfer through the dock, the dock may further include a data transfer cable such as, but not limited to USB or Thunderbolt or Ethernet directly coupled to a computing device.

The infusion pump 112 included in the monitor system 100 includes a tubing 120 that is in connected to a reservoir 118 within the infusion pump 112. Other characteristics of the infusion pump include a display 114 and a user interface 116. In some embodiments the display 114 is a touchscreen thereby making the display 114 an integrated component of the user interface 116. The infusion pump 112 can further include a radio transmitter and receiver that enables wireless communication. In some embodiments the radio transmitter is a standard off the shelf BLUETOOTH radio that includes the BLUETOOTH LOW ENEGRY profile. In other embodiments a custom secure radio transmission system is used. The radio transmitter within the infusion pump 112 enables wireless transmission with the electronics package 108 thereby allowing sensor data to shown on the display 114.

Transmission of sensor data to the infusion pump 112 further enables real-time glucose monitoring which can further enable low-glucose suspend functionality. In these embodiments if the sensor data indicates a blood sugar level below a specified threshold, the infusion pump 112 can suspend delivery of basal insulin. In some embodiments the raw sensor data measured by the sensor 102 is manipulated or processed using the processor within the electronics package 108 to determine sensor data from interstitial fluid that corresponds to a blood glucose level. In still other embodiments, the electronics package 108 transmits the raw sensor data to the insulin pump 112 where the raw sensor data is processed to correspond to a blood glucose level. In still other embodiments, the electronics package 108 transmits both the raw sensor data and a first calculated blood glucose level to the insulin pump. In these embodiments the insulin pump can then use a different algorithm to calculate a second blood glucose level from the raw sensor data. The second blood glucose level then being used in conjunction with the first blood glucose level to determine a third calculated blood glucose level.

Further description regarding the sensor and associated sensor set can be found in U.S. Pat. No. 6,248,067, entitled ANALYTE SENSOR AND HOLIER-TYPE MONITOR SYSTEM AND METHOD OF USING THE SAME, U.S. Pat. No. 5,586,553, entitled TRANSCUTANEOUS SENSOR INSERTION SET, and U.S. Pat. No. 5,594,643, entitled DISPOSABLE SENSOR INSERTION ASSEMBLY, all of which is herein incorporated by reference.

Figure 2A:
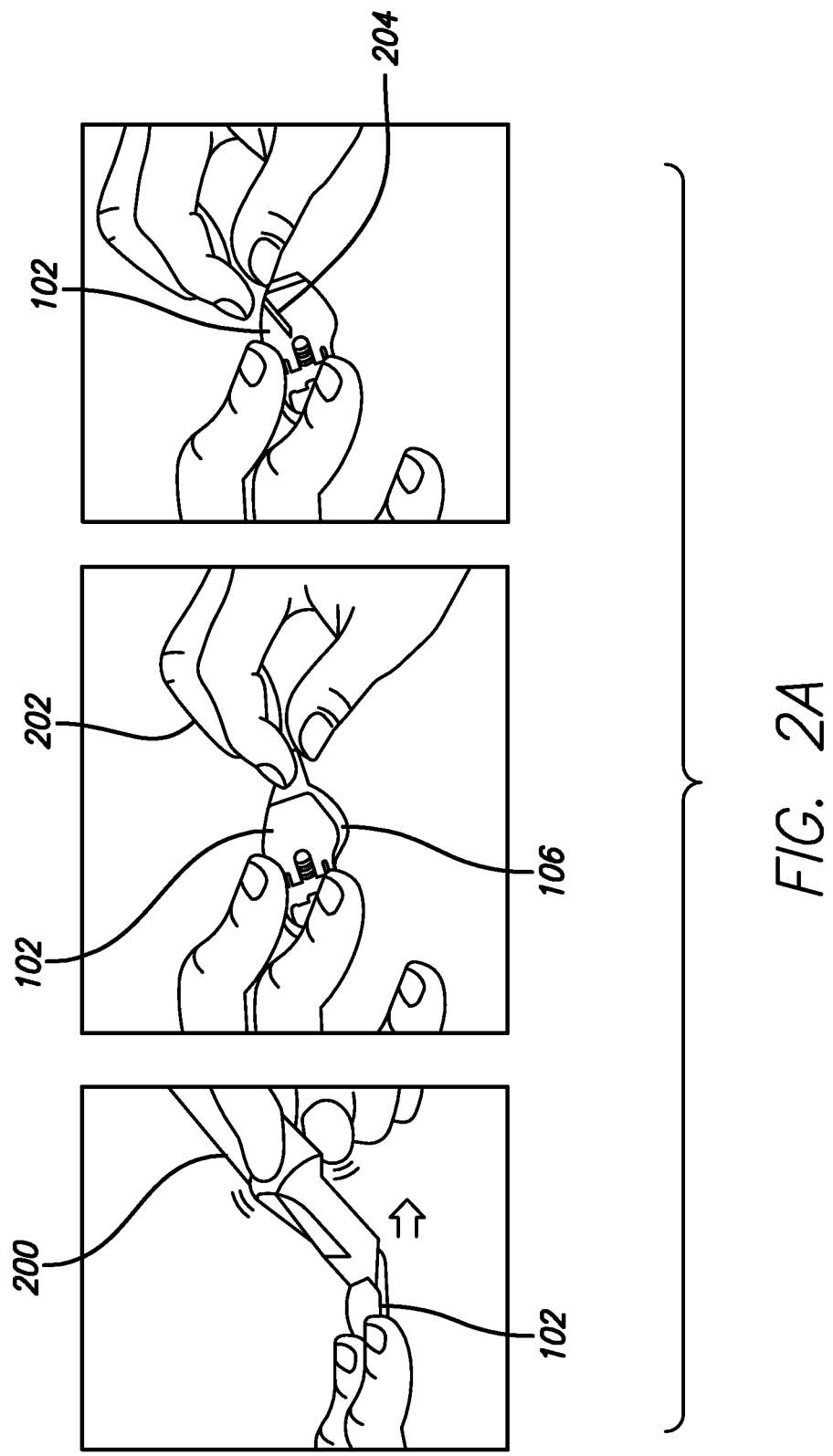
FIGS. 2A-2C are exemplary illustrations of placement of a sensor and installation of the electronics package onto the sensor, in accordance with embodiments of the present invention.
Figure 2B:
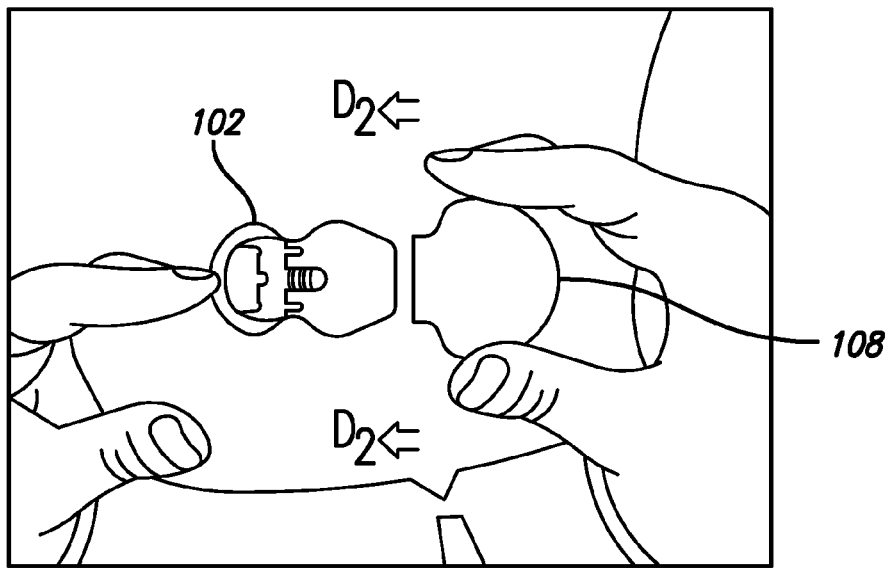
Figure 2C:
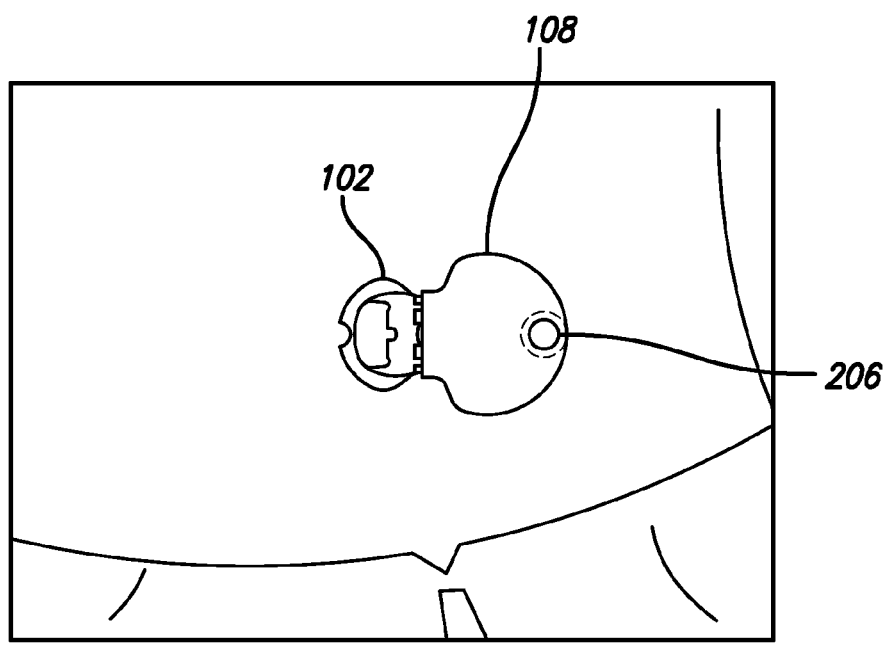

FIGS. 2A-2C are exemplary illustrations of placement of a sensor 102 and installation of the electronics package 108 onto the sensor 102, in accordance with embodiments of the present invention. FIG. 2A illustrates a sequence of typical steps used to place the sensor 102 within interstitial fluid of a patient. The leftmost panel of FIG. 2A is illustrative of using an inserter 200 to assist in the installation or placement of the sensor 102. Commonly, inserters 200 are customized to accommodate a specific type of sensor 102. For additional information regarding inserter 200 please see U.S. patent application Ser. No. 10/314,653 filed on Dec. 9, 2002, entitled INSERTION DEVICE FOR INSERTION SET AND METHOD OF USING THE SAME, U.S. Pat. No. 6,607,509, entitled INSERTION DEVICE FOR AN INSERTION SET AND METHOD OF USING THE SAME, and U.S. Pat. No. 5,851,197 entitled INJECTOR FOR A SUBCUTANEOUS INFUSION SET, all of which are herein incorporated by reference.

The middle panel of FIG. 2A is an illustration showing the removal of the adhesive backing 106 to expose an adhesive that enables adhesion of the sensor 102 to skin 202 of a patient. The rightmost panel of FIG. 2A is an illustration that depicts the removal of an introducer needle 204 that is used during the placement of the sensor 102. FIG. 2B is an exemplary illustration showing the installation of the electronics package 108 onto the sensor 102. Direction arrows $D_2$ indicate that the electronics package 108 is pushed onto the sensor 102 that was adhered to the patient, as shown in the middle panel of FIG. 2A. In some embodiments, it is desirable to wait a predetermined period of time before installing the electronics package 108 onto the sensor 102. For example, it may be advantageous to wait for up to 15 minutes for the sensor 102 to be properly hydrated or wetted by the patient's interstitial fluid before attaching the electronics package 108. In other embodiments it may take longer or less time before is sensor is considered properly hydrated. Being able to detect if an installed sensor 102 is properly hydrated can be used by a practitioner to help determine if the sensor was properly installed into the interstitial fluid. In other embodiments there is no minimum time required before attaching the electronics package 108 to the sensor 102. In still more embodiments, the sensor 102 need not be hydrated before the electronics package 108 is connected. And in additional embodiments, the electronics package 108 may be integrated with the sensor before the sensor is inserted into a user. Once the electronics package 108 is coupled with the sensor 102 some embodiments initialize the sensor based on algorithms stored in the electronics package. During the initialization process algorithms can determine if the sensor is properly hydrated and will most likely function as designed. In other embodiments initialization of the sensor is not required.

As illustrated in FIG. 2C, some embodiments of the electronics package 108 include a feedback indicator 206. In one embodiment the feedback indicator 206 is a light emitting diode (LED) that can be seen through a translucent or semi-translucent housing. In other embodiments, different light elements can be used, such as, but not limited to incandescent lights, fluorescent lights, organic light emitting diodes (OLED) or the like. In still other embodiments, the feedback indicator 206 can be an audible tone or a vibration alarm similar to those in mobile phones. In embodiments with the feedback indicator 206, the electronics package 108 can provide feedback regarding the hydration level of a connected sensor. For example, the recorder includes hardware and software that can determine if the sensor 102 is properly hydrated. The feedback indicator 206 can help a practitioner by narrowing the type of troubleshooting that needs to be performed. For example, the feedback indicator 206 can be programmed to flash a specific sequence or color to indicate that the sensor 102 is properly hydrated. Similarly, the feedback indicator 206 can be programmed to flash a different sequence or color to indicate that the sensor is not properly hydrated. In other embodiments, the feedback indicator 206 can further be programmed to flash a particular sequence or color that indicates to a practitioner that the electronics package 108 is not fully charged or even that data needs to be transferred from the electronics package 108 before additional data can be recorded. The examples provided are not intended to be exhaustive of conditions that can be reported by the feedback indicator 206. The particular examples provided are intended to be exemplary and should not be construed as limiting the scope of the present invention.

Figure 3:
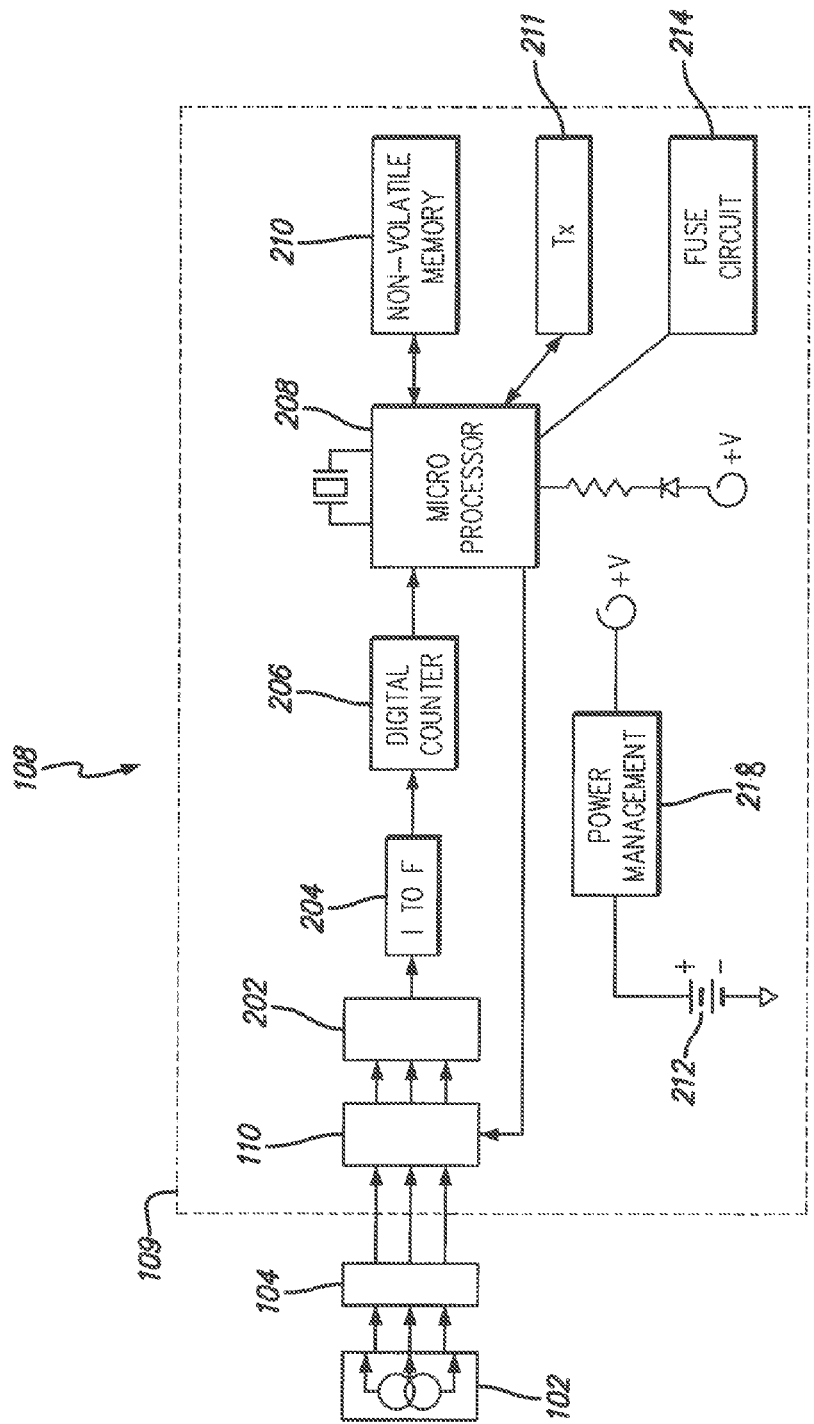
FIG. 3 is an exemplary block diagram illustrating components within the electronics package, in accordance with one embodiment of the present invention.

FIG. 3 is an exemplary block diagram illustrating components within the electronics package 108, in accordance with one embodiment of the present invention. A power supply 212 connected to power management 218 is found within the package housing 109 of the electronics package 108. In some embodiments the power supply 212 is a battery assembly that uses a rechargeable battery chemistry to provide power to the electronics package 108. In one embodiment the power supply 212 is made up of lithium ion battery cells. However, it is understood that alternate battery chemistries may be used, such as nickel metal hydride, alkaline or the like. Similarly, various embodiments can use a single battery cell for a shorter life such as for a single-use disposable unit while other embodiments use multiple battery cells that enable longer and/or reusable/rechargeable units.

In rechargeable embodiments the power management 218 includes circuitry and programming to allow recharging of the power supply 212 via the package port 110. In some embodiments power management 218 also includes circuitry and programming that enables a low battery warning alarm. In some embodiments the power supply 212 is capable of enabling the electronics package 108 to measure and/or record data for six days with a factor of safety of one additional day. Additionally, after six or seven days of measuring or recording data, the power supply further enables operation of an integrated clock in the electronics package 108 for an additional seven days. Alternative embodiments may provide longer or shorter battery lifetimes, or include a power port or solar cells to permit recharging of the power supply 212.

The sensor 102 is connected via the connector 104 and the package port 110 to a signal conditioning circuit 202, such as a potentiostat or the like, in the package housing 109 of the electronics package 108. The signal conditioning circuit 202 is in turn connected to a current to frequency converter (I to F) 204. The output of the current to frequency converter 204 is a digital frequency that varies as a function of the sensor signal produced by the sensor 102. In alternative embodiments, other signals, such as voltage, or the like, may be converted to frequency. In one embodiment, the digital frequency is then counted by a digital counter 206, and a value from the digital counter 206 is periodically read and stored with an indication of elapsed time, by a microprocessor 208, into a non-volatile memory 210. In other embodiments the value from the digital counter 206 is sent to transmitter 211 for transmission to, but not limited to, the infusion pump (not shown). In further embodiments the transmitter 211 additionally functions as a receiver thereby allowing two way communication between the electronics package 108 and the infusion pump.

In some embodiments, the electronics package 108 provides power to drive the sensor 102 via the package port 110 and the connector 104. Power from the electronics package 108 may also be used to speed initialization of the sensor 102, when it is first placed under the skin. The use of an initialization procedure can result in a sensor 102 providing stabilized data in an hour or less compared to requiring several hours before stabilized data is acquired without using an initializing procedure. One exemplary initialization procedure uses a two step process. First, a high voltage (preferably between 1.0-1.2 volts—although other voltages may be used) is applied to the sensor 102 for one to two minutes (although different time periods may be used) to initiate stabilization of the sensor 102. Then, a lower voltage (preferably between 0.5-0.6 volts—although other voltages may be used) is applied for the remainder of the initialization procedure (typically 58 minutes or less). The initialization procedure described above is exemplary and other initialization procedures using differing currents, voltages, currents and voltages, different numbers of steps, or the like, may be used. In all embodiments the microprocessor 208 is further coupled to a fuse circuit 214. The fuse circuit 214 can be used to help limit the number of uses of the sensor thereby ensuring sensors are not used beyond their expected lifecycle. Use of a sensor beyond its expected lifecycle can lead to erroneous and unreliable readings that may compromise the efficacy of therapy. Additional details regarding the fuse circuit will be discussed below.

Figure 4A:
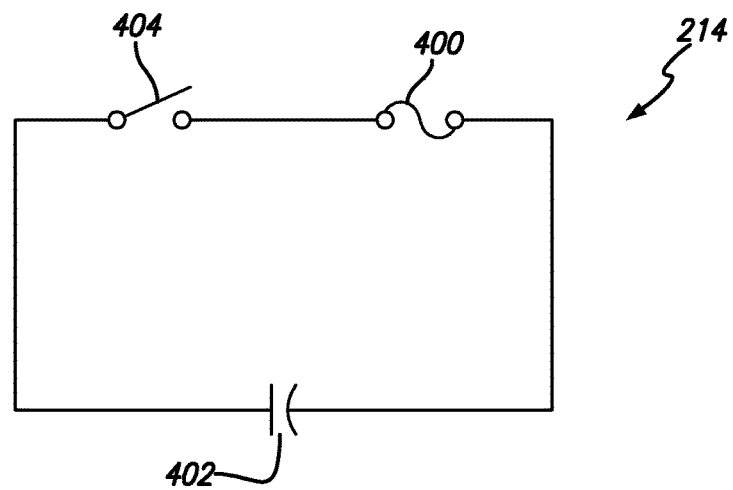
FIGS. 4A-4D are exemplary views of the fuse circuit in accordance with embodiments of the present invention.
Figure 4B:
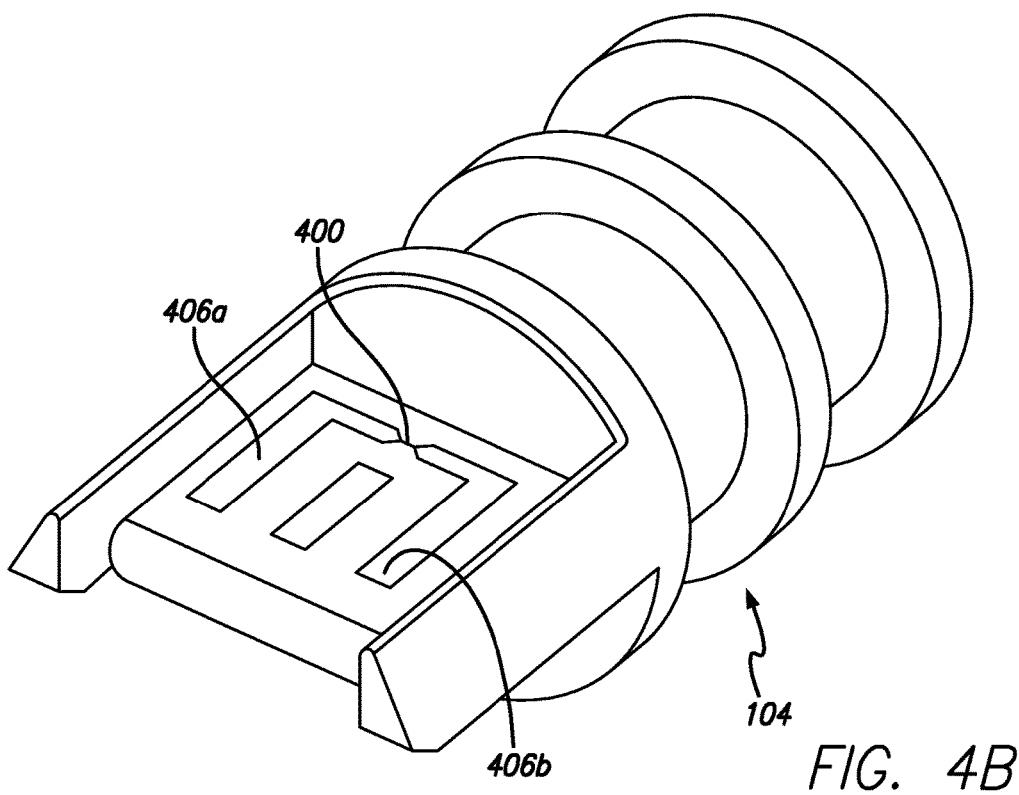

FIGS. 4A-4D are exemplary views of the fuse circuit 214 in accordance with embodiments of the present invention. FIG. 4A illustrates a basic circuit diagram with switch 404 that is controlled by the microprocessor 208. The charging of capacitor 402 would likewise be controller by the microprocessor 208. Upon closing the switch 404 the capacitor 402 would discharge with enough energy to break fuse 400. FIG. 4B illustrates elements of the fuse circuit that are implemented on the connector 104 from FIG. 1. As illustrated, fuse 400 is made by narrowing material that also makes up sensor detection pads 406a and 406b. The sensor detection pads 406a and 406b being shorted by fuse 400 serve as a switch that signals to the electronics package that a sensor is plugged in. In some embodiments, upon detecting the sensor, the electronics package initiates a timer for a first specified time. Once the first specified time has elapsed the capacitor 402 is charged and discharged into the shorted sensor detection pads 406a and 406b thereby breaking the fuse 400. In some embodiments the sensor signals can continue until the sensor is disconnected or until a second specified time has elapsed. The breaking of the short between sensor detection pads 406a and 406b can ensure that the sensor is only used once as the microprocessor can perform a check for shorted sensor detection pads 406a and 406b upon initialization of a sensor.

Figure 4C:
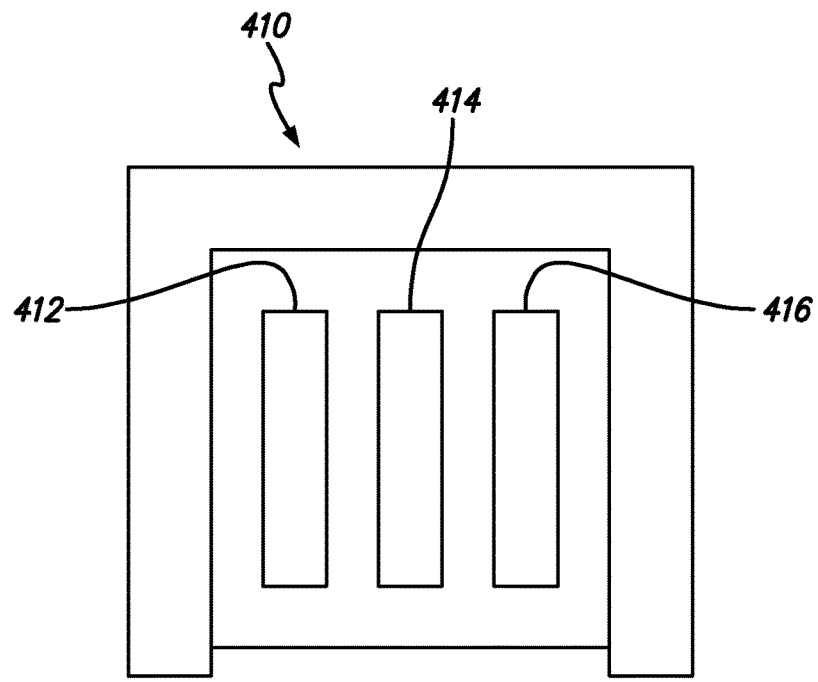
Figure 4D:
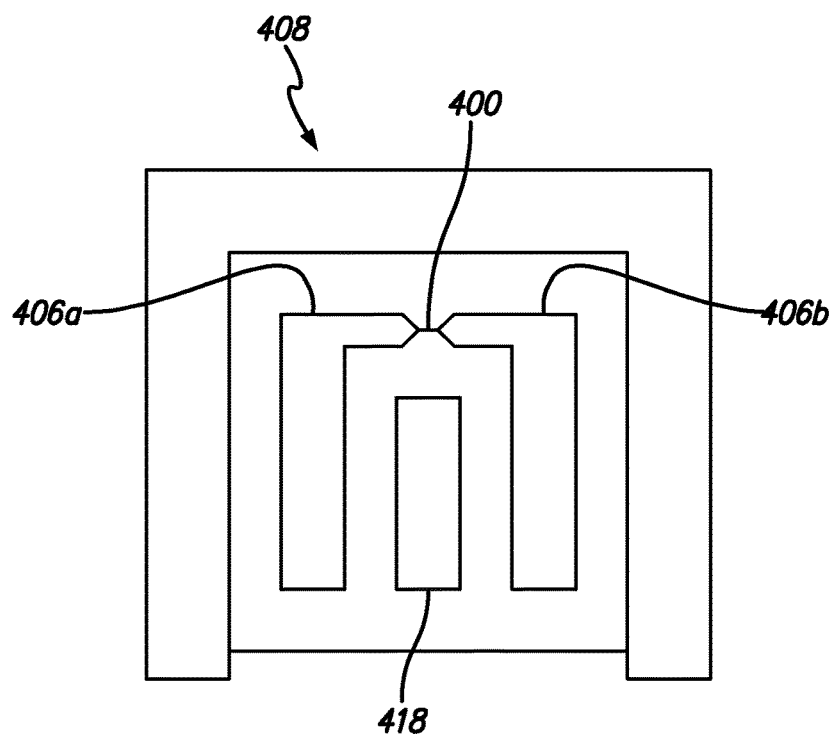

FIGS. 4C and 4D are illustrations of a first side 408 and a second side 410 of the connector 104, in accordance with an embodiment of the present invention. The first side 408 includes the previously discussed sensor detection pads 406a and 406b along with fuse 400. Located between the sensor detection pads 406a and 406b is an electrical contact for a second working electrode 418. On the second side 410 of the connector 104 are the contacts for a counter electrode 412, a first working electrode 414 and a reference electrode 416. The relative position of the contacts should not be construed as limiting as the various locations can vary depending on how traces are made on the sensor.

FIG. 5A is an exemplary illustration of package port 110 that would receive the connector 104 from the sensor, in accordance with one embodiment of the present invention. The embodiment shown in FIG. 5A is a 10-pin connector that enables communication with the contact pads discussed in FIGS. 4A-4D while also providing additional electrical contacts for power, transmitters and receivers. The particular embodiments discussed in detail below should not be construed as limiting. Other embodiments can use various port and pin configurations. In still other embodiments, additional or fewer electrical contacts may be implemented on both the package port and the connector to enable or disable various sensor features. As shown in FIG. 5A pins 506a and 506b are designed to interface with sensor detection pads 406a and 406b. Likewise, second working electrode pin 518 interfaces with second working electrode contact 418. Counter pin 512, first working electrode pin 515 and reference pin 516 interface respectively with counter contact 412, first working electrode contact 415 and reference contact 416. Further included are ground pin 502, charge pin 504, transmitter pin 510 and receiver pine 516. For single-use embodiments, the charge pin 504 can be omitted.

Figure 5B:
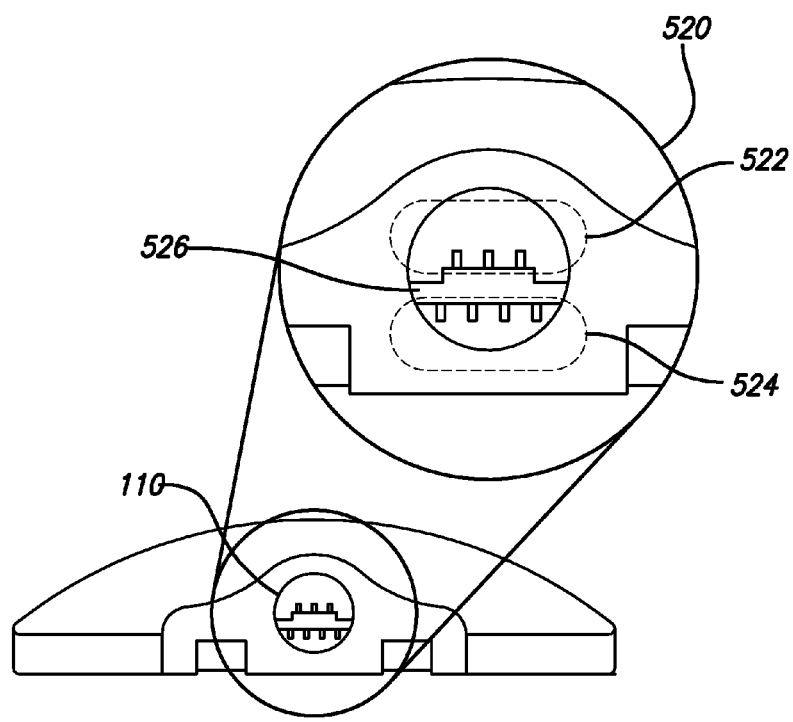
FIGS. 5B-5D illustrate various embodiments of detail of the recorder port, in accordance with embodiments of the present invention.
Figure 5C:
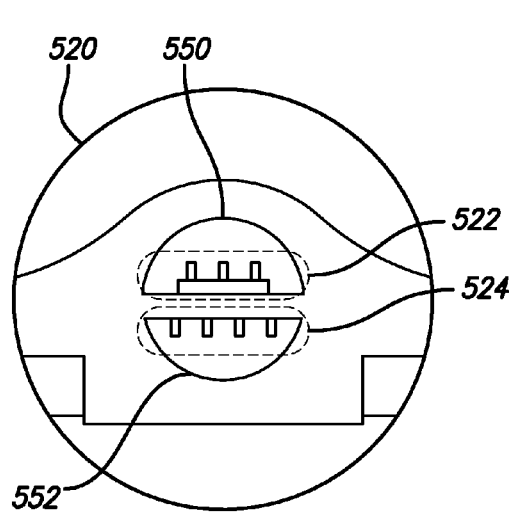
Figure 5D:
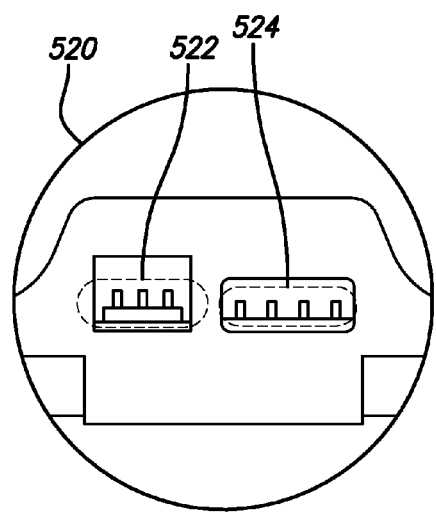

FIGS. 5B-5D illustrate various embodiments of detail 520 of the recorder port 110, in accordance with embodiments of the present invention. Detail 520 shows top contacts 522 and bottom contacts 524 which together can simply be referred to as "electronics package contacts". In the embodiment illustrated the electronics package contacts are mounted to a circuit board 526 to which the components described in FIG. 3 are also mounted. The electronics package contacts can be board mounted springs, or simple contact pads, or any other variety of contact that creates a reliable electrical connection.

The configuration illustrated is intended to be exemplary and should not be construed to be limiting. For example, in alternative embodiments shown in FIG. 5C, rather than a single recorder port 110 (FIG. 5A), the sensor 104 could have two separate ports with the first port 550 providing access to top contacts 522 while the second port 552 provides access to bottom contacts 524. Similarly, other embodiments could use two separate ports while placing the bottom contacts 524 on the same side of the circuit board 526 as the top contacts 522, as shown in FIG. 5D.

Figure 6:
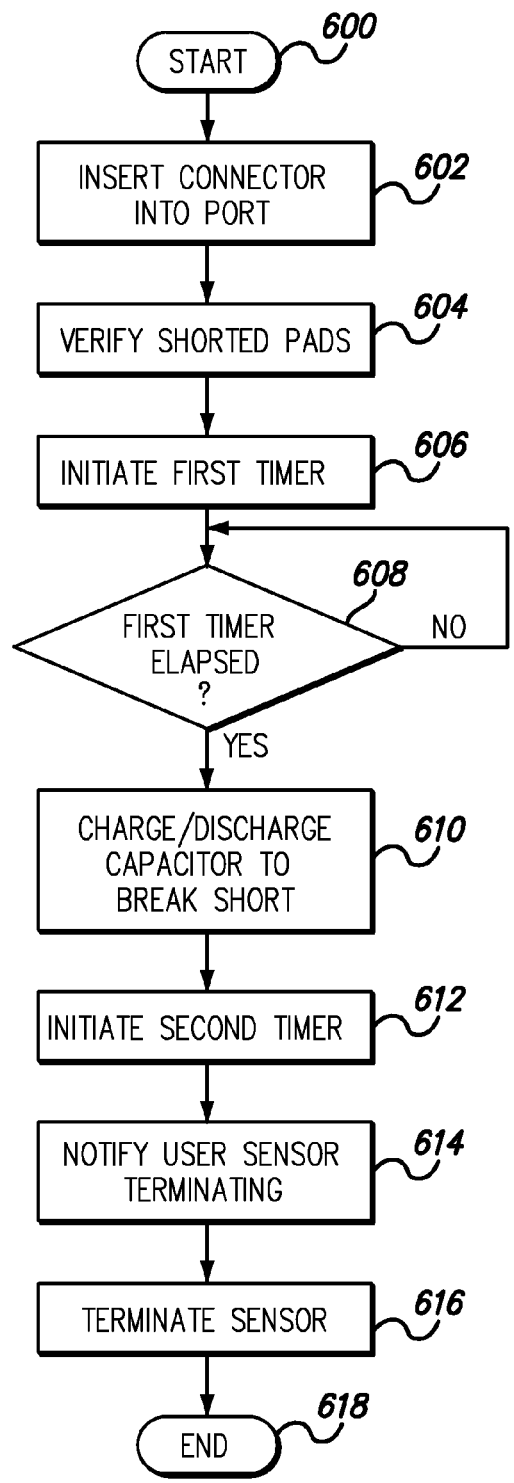
FIG. 6 is an exemplary flow chart illustrating operations to initiate a sensor with a fuse, in accordance with an embodiment of the present invention.

FIG. 6 is an exemplary flow chart illustrating operations to initiate a sensor with a fuse, in accordance with an embodiment of the present invention. The flow chart begins with START operation 600 followed by operation 602 where the connector for the sensor is inserted into the package port. Operation 604 utilizes the microprocessor within the electronics package to verify a short between the sensor detection pads. Operation 606 initiates a first timer and operation 608 determines if the first timer has reached the predetermined elapsed time. In some embodiments, the first timer allows the sensor to be used for 138 hours. In other embodiments, shorter or longer periods may be used for the first timer depending on the chemistry and configuration of the sensor.

Operation 610 charges and discharges the capacitor within the fuse circuit to break the fuse and open the short between the sensor detection pads. Operation 612 starts a second timer that is programmed to stop the sensor from functioning after a specific time has elapsed. In one embodiment, the second timer is set to run for six hours. Together with the initial 138 hours, this embodiment results in 144 hours, or six days of sensor use. In other embodiments, six days of sensor use may also be the total number of days of use but various times can be used for the first timer and second timer to ensure the sensor does not cease functioning while a user is asleep. Accordingly, the first time period may be shortened in order to increase the second time period while still having the sensor operate for six days. In some embodiments the first and second timers are countdown timers that count down from the predetermined elapsed time to zero. In other embodiments, the first and second timers count forward until the elapsed time is the same as the predetermined elapsed time. In still other embodiments the first timer is a countdown timer and the second timer counts forward or vice versa. Operation 614 notifies the user via messages displayed on the infusion pump that disconnecting the sensor will permanently terminate use of the sensor. In some embodiments operation 614 further displays the amount of time remaining until the sensor stops functioning on the display of the infusion pump.

In still other embodiments, the feedback indicator on the electronics package may begin blinking or flashing upon activation of the second timer. In some embodiments the color of the flashing LED of the feedback indicator of the electronics package can change the longer the second timer is running. For example, upon initiation of the second time, the LED may flash a first color such as green. When about half the time of the second timer has elapsed, the LED switches to a second color such as yellow. Finally, when about a quarter of the time for the second timer remains, the LED switches to a third color such as, but not limited to, red. In addition to changes color, in other embodiments the LED feedback indicator on the electronics package can also flash at different rates depending on how much time of the second timer remains. Operation 616 terminates the sensor. In some embodiments the sensor may continue to operate, but signals from the sensor are not processed or transmitted to other devices. In other embodiments sensor functionality is terminated by disconnecting the power supply. Operation 618 ends the process.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A monitor system to record a characteristic of a user, the system comprising:
    a sensor to produce signals indicative of a glucose characteristic measured in the user, the sensor having a connector with a plurality of contacts, wherein at least one element of a fuse system is implemented on the connector, the at least one element of the fuse system comprising:
        at least two contacts shorted by a fuse trace, the fuse trace comprising narrowing material that also makes up the at least two contacts; and
    an electronics package that includes a package housing,
    a battery being contained within the package housing,
    a package port interfaced with the connector to receive the produced signals from the sensor,
    a fuse timer; and
    a package processor programmed to execute instructions of machine readable program code stored in non-volatile memory comprising:
        processing the signals from the sensor;
        storing the processed signals in non-volatile memory; and
        controlling the fuse system,
        wherein upon detecting that the package port is interfaced with the connector of the sensor, initiating the fuse timer for a specified time, and
        causing the fuse trace to be destroyed after the fuse timer reaches a threshold value.

2. A monitor system as described in claim 1, wherein the package processor is programmed to execute instructions further comprising initializing and confirming the sensor before the fuse timer is initiated.

3. A monitor system as described in claim 2, wherein the package processor is programmed to execute instructions further comprising initializing of the sensor in response to detecting the at least two contacts shorted by the fuse trace, the destruction of the fuse trace removing the short thereby preventing reuse and reinitialization of the sensor.

4. A monitor system as described in claim 3, wherein the fuse system further includes a capacitor.

5. A monitor system as described in claim 4, wherein the package processor is programmed to execute instructions further comprising causing the capacitor to charge prior to the fuse timer reaching the threshold value.

6. A monitor system as described in claim 5, wherein the package processor is programmed to execute instructions further comprising, upon reaching the fuse timer threshold value, causing the capacitor to be discharged to destroy the fuse trace.

7. A monitor system as described in claim 6, wherein upon destroying the fuse trace the electronics package initiates a second timer, the second timer having a limit of time before the sensor stops functioning.

8. A monitor system as described in claim 7, wherein an alarm indicates the second timer has been initiated, the alarm providing feedback until the limit of time has been reached and the sensor stops functioning.

9. A monitor system as described in claim 8, wherein the alarm is visual feedback provided by a flashing LED.

10. A monitor system as described in claim 9, wherein the package processor is programmed to execute instructions further comprising causing the color of the flashing LED to change from a first color indicative of the second timer being initiated, to a second color indicative of half the limit of time remaining, to a third color indicative of a last quarter of the limit of time remaining.

11. A monitor system as described in claim 10, wherein the package processor is programmed to execute instructions further comprising, during the last quarter of the limit of time remaining, causing the period between flashes of the LED to begin to shorten in proportion to an expiration of the second timer, thereby visually indicating with faster flashes that the second timer is nearing completion and the sensor will cease to function.

* * * * *